United States Patent [19]

Larson

[11] Patent Number: 5,282,793
[45] Date of Patent: Feb. 1, 1994

[54] SYRINGE HOLDER AND APPLICATOR

[76] Inventor: Eldon E. Larson, 7500 Seabeck-Holly Rd., Bremerton, Wash. 98312

[21] Appl. No.: 371,520

[22] Filed: Oct. 2, 1989

[51] Int. Cl.$^5$ ................................ A61M 5/32
[52] U.S. Cl. .................. 604/192; 604/198; 604/136
[58] Field of Search ............ 604/198, 187, 263, 136, 604/137

[56] References Cited

U.S. PATENT DOCUMENTS

| | | | |
|---|---|---|---|
| 3,880,163 | 4/1975 | Ritterskamp | 604/136 |
| 4,601,708 | 7/1986 | Jordan | 604/136 |
| 4,639,249 | 1/1987 | Larson | 604/198 |
| 4,787,891 | 11/1988 | Levin et al. | 604/136 |
| 5,141,496 | 8/1992 | Dalto et al. | 604/136 X |

Primary Examiner—John D. Yasko
Attorney, Agent, or Firm—H. M. Cross, Jr.

[57] ABSTRACT

The structure of the Syringe Holder and Applicator provides an inner cylindrical tube adapted to have a hypodermic syringe inserted and held therein. This inner tubular syringe holder is slideably contained within an outer cylindrical tube. A cylindrical coil-spring retainer tube is also contained within the outer tube at the distal end of the outer tube's cylindrical cavity, leaving a considerable portion of the outer tube's cylindrical cavity free for occupation by the inner tubular syringe holder. The body of the outer tube is provided with a trigger mechanism which will automatically engage and lock the inner tubular syringe holder in a retracted position within the outer tube's cylindrical cavity when the inner tubular syringe holder is retracted toward the distal end of the outer tube's cylindrical cavity. The trigger mechanism is designed to, when pressed inward, release the inner tubular syringe holder for travel within the outer tube's cylindrical cavity. A coil spring is positioned axially within the cylindrical coil-spring retainer tube and bears against the distal end of the inner tubular syringe holder to urge the tubular syringe holder toward the proximal end of the outer tube's cylindrical cavity. The coil spring and its cylindrical coil-spring retainer tube are so constructed and arranged, with respect to one another and with respect to the inner syringe tubular holder, that a hypodermic syringe barrel may be axially inserted in the proximal end of the coil-spring retainer tube and axially through the coil spring into the inner tubular syringe holder.

6 Claims, 3 Drawing Sheets

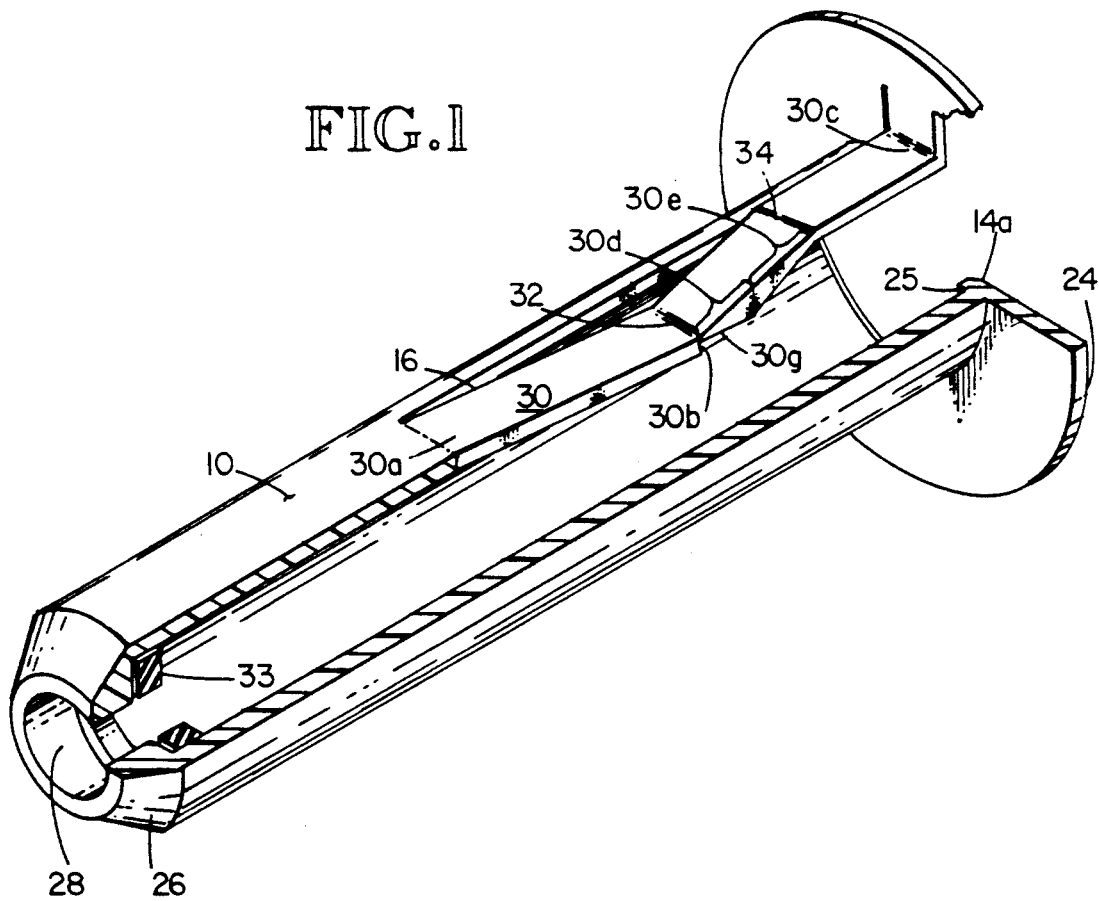

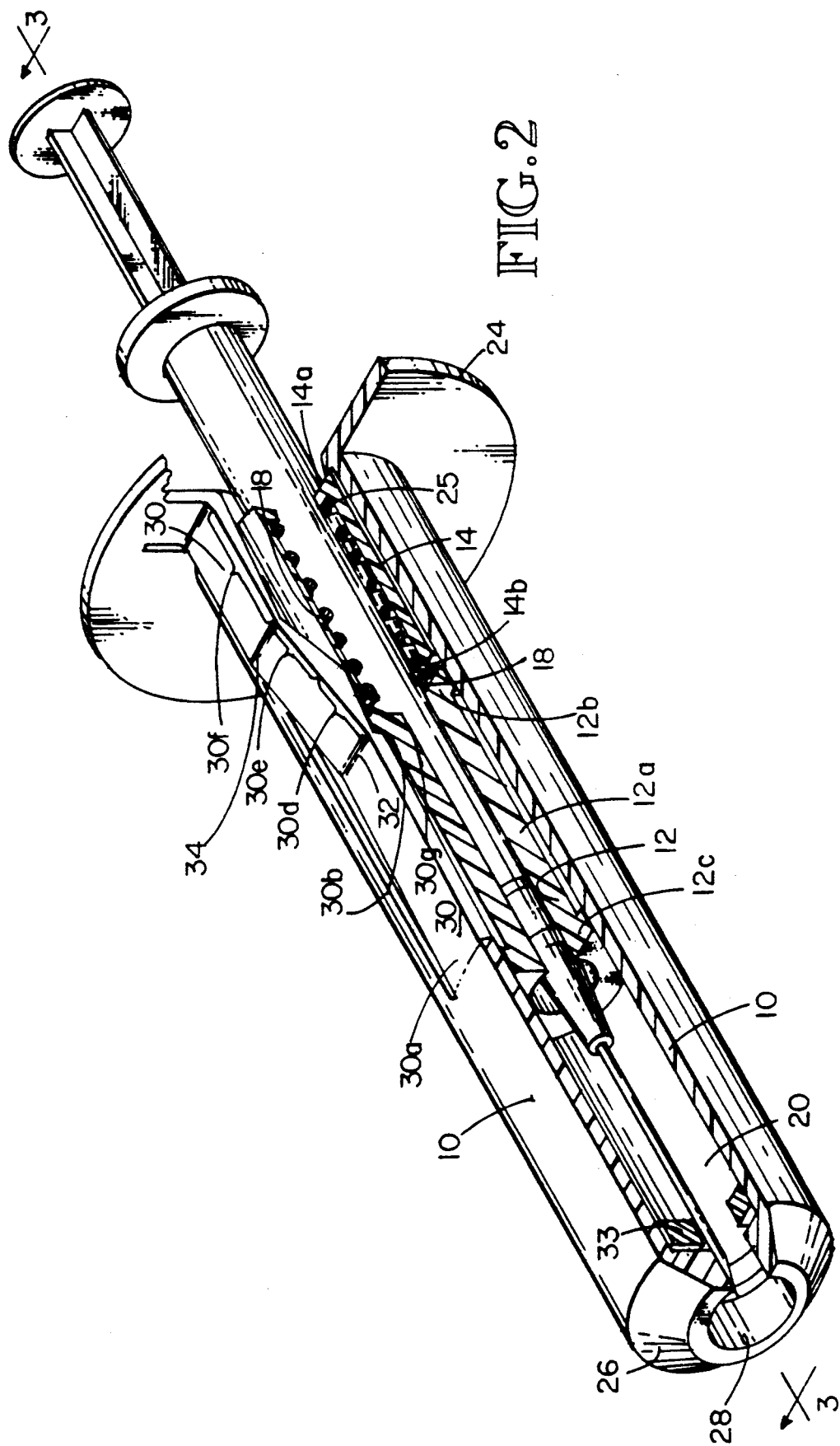

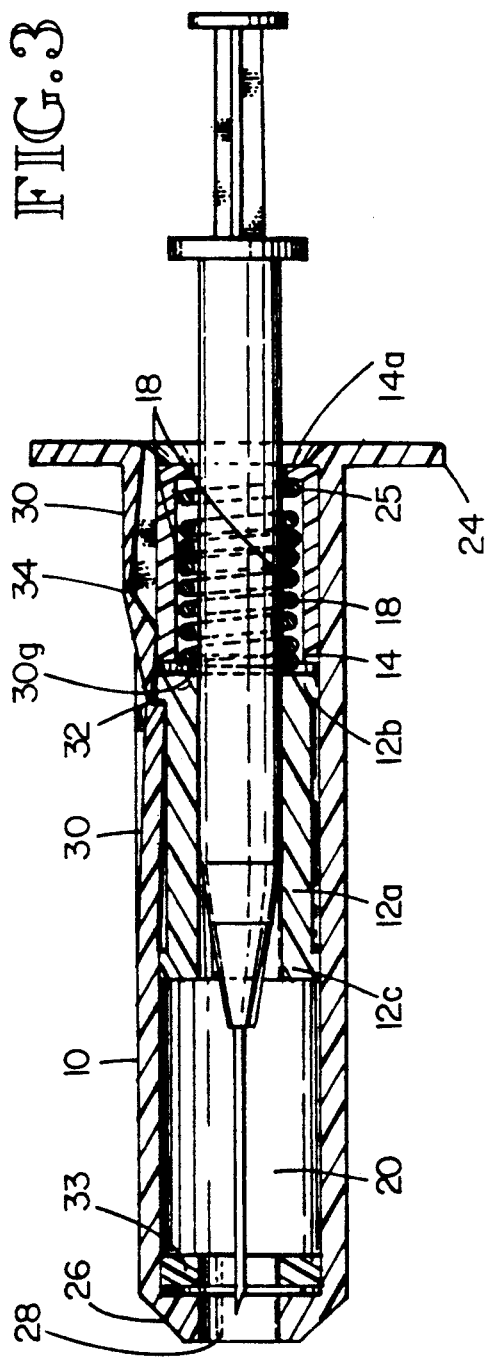

SYRINGE HOLDER AND APPLICATOR

FIELD OF THE INVENTION

This invention relates to syringe holders designed to hold hypodermic syringes and to automatically insert the syringe needle subcutaneously upon actuation of a trigger mechanism on the holder.

BACKGROUND OF THE INVENTION

So-called automatic-insertion syringe holders have been proposed for use with hypodermic syringes. Generally speaking, these prior art holders have been relatively costly to manufacture and, sometimes, awkward to use. Cost and difficulty of use are inhibitors to acceptance of such devices.

SUMMARY OF THE INVENTION

A primary object of the present invention is to provide a syringe holder that is suitable for safe and convenient use with a hypodermic syringe of the type used by diabetics. Another object is to provide such a holder fashioned to be inexpensive to manufacture, simple to assemble, and easy to operate.

These and other objects and advantages are obtained by the structure of the present invention. This structure provides an inner cylindrical tube adapted to have a hypodermic syringe inserted and held therein. This inner tubular syringe holder is slideably contained within an outer cylindrical tube. A cylindrical coil-spring retainer tube is also contained within the outer tube at the distal end of the outer tube's cylindrical cavity, leaving a considerable portion of the outer tube's cylindrical cavity free for occupation by the inner tubular syringe holder. The body of the outer tube is provided with a trigger mechanism which will automatically engage and lock the inner tubular syringe holder in a retracted position within the outer tube's cylindrical cavity when the inner tubular syringe holder is retracted toward the distal end of the outer tube's cylindrical cavity. The trigger mechanism is designed to, when pressed inward, release the inner tubular syringe holder for travel within the outer tube's cylindrical cavity. A coil spring is positioned axially within the cylindrical coil-spring retainer tube and bears against the distal end of the inner tubular syringe holder to urge the tubular syringe holder toward the proximal end of the outer tube's cylindrical cavity. The coil spring and its cylindrical coil-spring retainer tube are so constructed and arranged, with respect to one another and with respect to the inner syringe tubular holder, that a hypodermic syringe barrel may be axially inserted in the proximal end of the coil-spring retainer tube and axially through the coil spring into the inner tubular syringe holder.

BRIEF DESCRIPTION OF THE DRAWINGS

FIG. 1 is a perspective view of the outer cylindrical tube illustrating the structure of the trigger mechanism;

FIG. 2 is perspective partial view of the holder of this invention illustrating the relationship between the trigger mechanism, the inner tubular syringe holder, and the cylindrical coil spring retainer tube; and FIG. 3 is a partial cross section view further illustrating the operative parts of the invention.

DETAILED DESCRIPTION OF THE INVENTION

As illustrated by the Figures, the syringe holder of this invention comprises an outer cylindrical tube 10, an inner cylindrical tubular syringe holder 12, a cylindrical coil-spring retainer tube 14, an outer tube-mounted trigger mechanism 16, and a coil spring 18. The tubular members and the trigger mechanism are preferably made of injection-moldable plastic, the trigger mechanism preferably being an integral part of the outer tube 10. Coil spring 18 is preferably a steel compression spring.

The outer tube 10 is molded to provide an elongated tubular body that provides a cylindrical cavity 20 therein. The distal end 22 of the outer tube is open and surrounded by a circular flange 24. Flange 24 provides a finger grip. The proximal end 26 of the outer tube is tapered to a smaller diameter proximal opening 28. The molded outer tube is provided with the trigger mechanism 16 in the form of an arcuate narrow strip 30 that is integral at one end to the outer tube body and integral at the other end to the outer tube circular flange 24.

The sides of the trigger mechanism strip 30 are adjacent to but separate from the main portion of the outer tube body. The strip 30 has a first portion 30a that extends from the outer tube body distally to an interior step 30b, and a second portion 30c that extends distally from step 30b to the outer body circular flange 24. Strip 30 is formed during the molding process such that the first portion 30a is of the same thickness as the thickness of the main outer tube body portion and its outer and inner surfaces are naturally angled downwardly. Strip 30 is formed during the molding process such that the second portion 30c has a varying thickness and is naturally angled upwardly; being quite thin adjacent step 30b, being first increasingly thicker away from step 30b (in region 30d) and then increasingly thinner (in region 30e), being quite thin again at the terminus of region 30e, and being either of the same thickness as the thickness of the main outer tube body portion for the balance of its extent (region 30f) or being of increasing thickness from the terminus of region 30e to flange 24. The outer surface of the strip second portion 30c naturally angles upwardly more steeply in regions 30d and 30e, and then angles upward less steeply to the point of joinder with the circular flange 24; being raised above the main outer tube body portion in region 30f. Step 30b provides an axial arcuate inner surface, or land, 30g that is extended distally, resulting in the increasingly thick portion 30d. The quite thin section of strip 30 adjacent step 30b provides a hinge line 32 so that the strip portions 30a and 30c can flex, relative to one another, at that hinge line 32. The quite thin section of strip 30 at the terminus of region 30e provides a second hinge line 34 so that the strip portions 30e and 30f can flex, relative to one another, at that hinge line 34.

Cylindrical coil-spring retainer tube 14 has an outer diameter just slightly smaller than the inner diameter of the outer tube 10; the coil-spring retainer tube 14 being able to be inserted into the outer tube cylindrical cavity 10. The outer tube circular flange 24 is provided with an inner circumferential lip 25, having an inner diameter only slightly smaller than the diameter of the outer tube cylindrical cavity 10, as a retainer to keep retainer tube 14 from sliding out after it has been forced into cavity 10. Retainer tube 14 has a distal end partially closed by annular end wall 14a, end wall 14a serving as a coil spring stop for coil spring 18. Retainer tube 14 has a proximal end 14b open to the outer tube cylindrical cavity 20. Coil spring 18 extends from its stop 14a, through retainer tube 14 and extends beyond the retainer tube proximal end 14b to butt against the outer distal end of the inner tubular syringe holder 12.

Inner tubular syringe holder 12 has a cylindrical main body portion 12a and distal and proximal end rims 12b and 12c that extend outward beyond the surface of portion 12a. Rims 12b and 12c have outer diameters just slightly smaller than the inner diameter of the outer tube cylindrical cavity 20, and main body portion 12a has an outer diameter sufficiently less than the inner diameter of outer tube 10 that the inner edge of the trigger mechanism strip step 30b can ride along the outer surface of portion 12a. The depth of distal end 12b is about the same as the thickness of step 30b and consequently, when inner tubular syringe holder 12 is positioned in the retracted position shown in FIG. 3, step 30b will abut the distal end 12b and lock the holder 12 in that position.

The outer diameters of holder rims 12b and 12c and of retainer tube 14 are the same. The land 30g on the inner surface of trigger mechanism strip 30 bears against the outer surface of retainer tube 14. By pressing radially inward on the second portion 30c of strip 30, at about its midpoint (i.e. at the second; hinge line 34), the distal edge of land 30g will engage retainer tube 14 and force the first portion 30a of strip 30 outward, the first and second portions 30a and 30c bending relative to one another about hinge line 32, and step 30b will be raised out beyond rim 12b of holder 12 to release holder 12 for axial movement toward the proximal end of the outer tube cylindrical cavity 20. The provision of the two hinge lines 32 and 34 permit portion 30c to rock on the distal edge of land 30g with the areas adjacent hinge lines 32 and 34 becoming flatter across their respective hinge lines. As portion 30c rocks, upon hinge line 34 being depressed inward, hinge line 32 is raised and carries the step 30b radially outward. The coil spring 18, compressed in retainer tube 14, will urge the syringe holder 12 toward the proximal end of the outer tube cylindrical cavity 20 upon release of the step 30b from engagement with rim 12b. The length of the outer tube 10 will be such that the syringe needle will be extended outward beyond the proximal end 26 of the outer tube 10. Because the spring force of the released coil spring 18 will urge the syringe holder 12 rapidly toward the proximal end, a cushion ring 33 is provided in the proximal end of the outer tube cylindrical cavity 20 to absorb the energy of the syringe as it impacts the proximal end of the outer tube 10.

The position of step 30b with respect to retainer tube 14 and syringe holder 12 must be such that a gap will exist when the syringe holder 12 is locked in its retracted position. When syringe holder 12 has been released, in order to bring it back into a position where the step 30b can re-engage distal rim 12b, the syringe holder 12 must be brought back further than the position that it will assume in its locked configuration. The gap mentioned above must be sufficient to enable this overtravel so that trigger mechanism strip 30 can spring inward to re-engage step 30b with rim 12b.

To load a syringe into the holder of this invention, the trigger mechanism would be first tripped so that syringe holder 12 would be released. Then a syringe would be located axially into the outer tube 10 from the distal end, the syringe being inserted until firmly lodged in the syringe holder 12. The syringe would then be drawn distally to shift the syringe holder 12. When the syringe holder 12 abuts the proximal end of the retainer tube 14, the syringe can be released because the locking step 30b will have dropped inward against the syringe holder main body portion 12a, ready to engage syringe holder rim 12b to lock the syringe holder 12 in its retracted position. The inner diameter of the syringe holder 12 must be such that an interference fit is created between the syringe barrel and the syringe holder that will enable the syringe holder 12 to be retracted against the compression force of the coil spring 18 without unintentional separation. This interference fit, however, must not be so tight that a spent syringe could not be removed and a fresh syringe substituted.

While the preferred embodiment of the invention has been described herein, variations in the design may be made. The scope of the invention, therefore, is only to be limited by the claims appended hereto.

The embodiments of the invention in which an exclusive property is claimed are defined as follows:

1. A syringe holder and applicator which comprises an outer cylindrical tube having a distal end into which a syringe may be inserted manually and having a proximal end through which a syringe needle may be extended automatically; an inner tubular syringe holder slideably fitted within said outer tube for axial movement in a cylindrical cavity provided by said outer tube, said tubular syringe holder having a distal end oriented toward the distal end of said outer tube and having a proximal end oriented toward the proximal end of said outer tube, and said tubular syringe holder being adapted to receive and hold the barrel of a syringe that has been inserted through the distal end of said outer tube into said tubular syringe holder with the syringe needle protruding through the proximal end of said of said tubular syringe holder; a coil spring member positioned within said cylindrical cavity axially of said tubular syringe holder and extending between the distal end of said outer tube and the adjacent distal end of said inner tubular syringe holder whereby positioning of said tubular syringe holder in a retracted position will result in compression of said coil spring; a trigger means integral with said outer tube, said trigger means having a first portion extending toward the distal end of said outer tube, said first portion having a locking element inclined inward to engage a portion of said tubular syringe holder to lock said tubular syringe holder in a retracted position toward the distal end of said cylindrical cavity when said tubular syringe holder is moved axially to that retracted position; said trigger means having another portion integral with and extending from said first portion toward the distal end of said outer tube and inclined outward toward the distal end of said outer tube, said second portion being so constructed and associated with said first portion that radially inward pressure on said second portion will result in said first portion being moved radially outward to release said locking element from a locking relationship with said tubular syringe holder to release said tubular syringe holder whereby said tubular syringe holder will be permitted to travel axially toward the proximal end of said outer tube under the force of said coil spring; and a cylindrical coil-spring retainer tube axially fitted within said outer tube, said retainer tube having a distal end positioned adjacent the distal end of said outer tube and having a proximal end oriented toward the proximal end of said outer tube, and said retainer tube extending from the distal end of said outer tube toward said tubular syringe holder, said coil spring being positioned within said retainer tube and seating against the retainer tube distal end and extending through the retainer tube proximal end into abutment with said tubular syringe holder; said trigger means comprising a strip integral with said outer tube, said trigger strip being integral at its ends with said outer tube and free to flex inward and outward with respect to said outer tube along the length of said strip, said first portion comprising the proximal half of said strip and said second portion comprising the distal half of said strip, and said strip having a hinge line thereacross between the two portions whereby said two portions may flex with respect to one another about said hinge line.

2. The holder of claim 1 wherein said strip second portion is provided with an inner land surface adjacent to said hinge line and contacting said coil-spring retainer tube whereby application of inward pressure on said second portion will cause said land surface to bear against said coil-spring retainer tube and raise said hinge line upward causing said second portion to flex upward and disengage said tubular syringe holder.

3. The holder of claim 2 wherein said strip second portion is provided with a second hinge line thereacross at a point distally of said inner land surface whereby application of said inward pressure will cause said second hinge line to deflect inward and cause said first hinge line to deflect outward, thereby rocking said land surface to effect a radially-outward shift of said locking element out of locking engagement with said tubular syringe holder.

4. A syringe holder and applicator which comprises an outer cylindrical tube having a distal end into which a syringe may be inserted manually and having a proximal end through which a syringe needle may be extended automatically; an inner tubular syringe holder slideably fitted within said outer tube for axial movement in a cylindrical cavity provided by said outer tube, said tubular syringe holder having a distal end oriented toward the distal end of said outer tube and having a proximal end oriented toward the proximal end of said outer tube, and said tubular syringe holder being adapted to receive and hold the barrel of a syringe that has been inserted through the distal end of said outer tube into said tubular syringe holder with the syringe needle protruding through the proximal end of said of said tubular syringe holder; a coil spring member positioned within said cylindrical cavity axially of said tubular syringe holder and extending between the distal end of said outer tube and the adjacent distal end of said inner tubular syringe holder whereby positioning of said tubular syringe holder in a retracted position will result in compression of said coil spring; a trigger means integral with said outer tube, said trigger means having a first portion extending toward the distal end of said outer tube, said first portion having a locking element inclined inward to engage a portion of said tubular syringe holder to lock said tubular syringe holder in a retracted position toward the distal end of said cylindrical cavity when said tubular syringe holder is moved axially to that retracted position; said trigger means having another portion integral with and extending from said first portion toward the distal end of said outer tube and inclined outward toward the distal end of said outer tube, said second portion being so constructed and associated with said first portion that radially inward pressure on said second portion will result in said first portion being moved radially outward to release said locking element from a locking relationship with said tubular syringe holder to release said tubular syringe holder whereby said tubular syringe holder will be permitted to travel axially toward the proximal end of said outer tube under the force of said coil spring; said trigger means comprising a strip integral with said outer tube, said trigger strip being integral at its ends with said outer tube and free to flex inward and outward with respect to said outer tube along the length of said strip, said first portion comprising the proximal half of said strip and said second portion comprising the distal half of said strip, and said strip having a hinge line thereacross between the two portions whereby said two portions may flex with respect to one another about said hinge line.

5. The holder of claim 4 wherein said strip second portion is provided with an inner land surface adjacent to said hinge line and contacting said coil-spring retainer tube whereby application of inward pressure on said second portion will cause said land surface to bear against said coil-spring retainer tube and raise said hinge line upward causing said second portion to flex upward and disengage said tubular syringe holder.

6. The holder of claim 5 wherein said strip second portion is provided with a second hinge line thereacross at a point distally of said inner land surface whereby application of said inward pressure will cause said second hinge line to deflect inward and cause said first hinge line to deflect outward, thereby rocking said land surface to effect a radially-outward shift of said locking element out of locking engagement with said tubular syringe holder.

* * * * *